United States Patent [19]

Koshikawa et al.

[11] Patent Number: 5,872,291
[45] Date of Patent: Feb. 16, 1999

[54] PROCESS FOR PRODUCING BENZOYL CHLORIDES

[75] Inventors: Takeshi Koshikawa; Toshihiro Hashimoto; Makoto Takagawa, all of Tsukuba, Japan

[73] Assignee: Mitsubishi Gas Chemical Company, Inc., Tokyo, Japan

[21] Appl. No.: 993,704

[22] Filed: Dec. 18, 1997

[30] Foreign Application Priority Data

Dec. 20, 1996 [JP] Japan .................................. 8-341438

[51] Int. Cl.⁶ ................................................. C07C 51/58
[52] U.S. Cl. ....................................................... 562/863
[58] Field of Search ............................................ 562/863

[56] References Cited

U.S. PATENT DOCUMENTS 3,274,242  9/1966  Etherington et al. .
3,894,923  7/1975  Grégoire .
5,599,981  2/1997  Fushimi et al. .

FOREIGN PATENT DOCUMENTS 647037A   10/1964  Belgium .
0723950   7/1996   European Pat. Off. .
2228049   11/1974  France .
10 39 053  3/1956  Germany .

*Primary Examiner*—Paul J. Killos
*Attorney, Agent, or Firm*—Armstrong, Westerman, Hattori, McLeland & Naughton

[57] ABSTRACT

Provided is a process for producing benzoyl chlorides which comprises reacting an aromatic aldehyde with chlorine in liquid phase in the presence of inert gas, whereby the generation of benzal chlorides by products whose separation is difficult can be suppressed.

6 Claims, No Drawings

PROCESS FOR PRODUCING BENZOYL CHLORIDES

BACKGROUND OF THE INVENTION

1) Field on the Invention

The present invention relates to a process for producing benzoyl chlorides useful as raw materials and intermediate products of agricultural chemicals, chemical synthetic products, etc.

2) Prior Art

Hitherto, as processes for producing benzoyl chlorides, a process for conducting hydrolysis of the corresponding trichloride and a process for chlorinating the corresponding aromatic carboxylic acid as raw material with a chlorinating agent such as thionyl chloride, phosphorus pentachloride, etc., have been known. U.S. Pat. No. 3,894,923 discloses a process for producing benzoyl chloride by reacting benzaldehyde having no side chain with chlorine.

Among them, when alkyl benzoyl chlorides are produced according to the process for conducting hydrolysis of the corresponding benzo trichlorides, it is very difficult to conduct selectively such reaction since alkyl benzo trichloride as the raw material is necessary and only one methyl group on alkyl benzene having at least two alkyl groups need be chlorinated selectively in order to obtain alkyl benzo trichloride.

Further, the process for chlorinating alkyl benzene carboxylic acid with thionyl chloride, etc., provides a high yield of acid chloride, but the use of the chlorinating agent requires a higher cost than the case of using chlorine as the raw material and causes many problems in respect of refining and post treatment.

U.S. Pat. No. 5,599,981 describes a process for producing alkyl benzoyl chloride in a high yield by reacting alkyl benzaldehyde with chlorine in a liquid phase in a comparatively low temperature. However, in the process for reacting an aromatic aldehyde with chlorine in a liquid phase, benzal chlorides are by-produced depending upon reaction conditions. For example, in U.S. Pat. No. 3,894,923 which discloses to obtain benzoyl chloride by reacting benzaldehyde with chlorine, about 0.3% of benzal chloride to benzoyl chloride has been by-produced.

It is difficult to separate the intended benzoyl chlorides from benzal chlorides in a conventional operation such as distillation since the boiling point of benzal chlorides is close to that of benzoyl chlorides. For example, the specific volatility of ethyl benzoyl chloride to 1-dichloromethyl-4-ethyl benzene as benzal chlorides is 1.1 or below.

Therefore, the separation between both in a conventional industrial distillation is very difficult.

It is not preferable that a large amount of such impurity is mixed in the intended benzoyl chlorides since benzoyl chlorides are utilized as raw materials of agricultural chemicals, etc.

Further, the longer the reaction time or the higher the concentration of aromatic aldehyde as raw material in the reaction liquid is, the more the amount of benzal chlorides to be by-produced is increased.

In the process for reacting an aromatic aldehyde with chlorine in a liquid phase, exothermic reaction occurs. Therefore, when benzoyl chlorides are produced with an industrial scale according to said process, the reaction time cannot be shortened to an extreme from the problem of removal of heat or the problem of operation. It is not preferable in an industrial production to lower the concentration of aromatic aldehyde as the raw material in the reaction liquid since production efficiency is lowered.

Thus, even in case where the reaction time is industrially suitable and the concentration of aromatic aldehyde as the raw material is high, a process for producing benzoyl chlorides to suppress by-production of benzal chlorides has been required.

SUMMARY OF THE INVENTION

An object to the present invention is to provide a process to suppress by-production of benzal chlorides in the process for producing benzoyl chlorides which comprises reacting an aromatic aldehyde with chlorine in liquid phase.

As a result of extensive studies of a process for producing benzoyl chloride under the above-mentioned prior art problems, the inventors have found that the generation of benzal chlorides as by-products whose separation is difficult can be reduced sharply by reacting an aromatic aldehyde with chlorine in liquid phase in the presence of inert gas, and accomplished the present invention.

That is, the present invention provides a process for producing benzoyl chlorides which comprises reacting an aromatic aldehyde with chlorine in liquid phase in the presence of inert gas.

DETAILED DESCRIPTION OF THE INVENTION

The present invention will be described in detail below.

The aromatic aldehyde to be used as the raw material in the present invention is a compound represented by the following general formula (I):

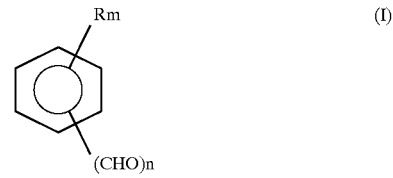

wherein R shows an alkyl group including methyl group, ethyl group, n-propyl group, isopropyl group, n-butyl group and isobutyl group, a phenyl group, an alkyl-substituted phenyl group, hydrogen or halogen including chlorine, etc, and m and n are integers of 1 to 5 showing the number of substituted group, $m+n \leq 6$, or a mixture of compounds represented by the same general formula (I) as defined above wherein R, m and n are the same as defined above and each R among the compounds is different from each other.

The benzal chlorides which are by-products of the reaction of the present invention are compounds of represented by the following general formula (II):

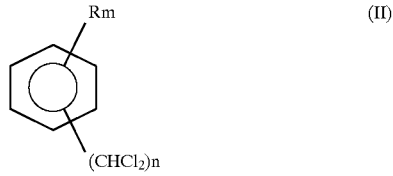

wherein R, m and n are the same as defined in the general formula (I).

or a mixture of compounds represented by the same general formula (II) as defined above wherein R, m and n are the same as defined above and each R among the compounds is different from each others.

Examples of the aromatic aldehyde include benzaldehyde, o-, m-, p- tolualdehyde, ethylbenzaldehyde, isopropylbenzaldehyde, isobutylbenzaldehyde, 2,6-dimethylbenzaldehyde, 2,4,5-trimethylbenzaldehyde, 4-phenylbenzaldehyde, (4-methylphenyl)benzaldehyde, etc., whereby the corresponding alkyl benzoyl chlorides are obtained according to the process of the present invention.

Regarding chlorine to be used in the present invention, when industrially available chlorine is used, it will be not limited. It is preferable to use dried chlorine. Usually, the reaction is carried out by bubbling the reaction solution with chlorine. In this case, feeding amount and feed rate of chlorine are not limited.

The inert gas to be used in the reaction is a gas inert to the reaction such as nitrogen, air, etc. The inert gas is fed to the reaction system in a mixture with chlorine or separately from chlorine. The feeding amount of inert gas is 0.1 to 50 times by mol and preferably, 1 to 10 times by mol to that of chlorine.

The reaction of the present invention can be conducted in the absence of a solvent or in the presence of a solvent inert to chlorination. Examples of the solvent include o-dichlorobenzene, chlorobenzene, carbon tetrachloride and benzonitrile.

The amount of the solvent is 0.5 to 100 parts by weight and, preferably, 1.0 to 50 parts by weight to 1 part by weight of aromatic aldehyde as the raw material.

The reaction of the present invention can be conducted in the absence of a catalyst. Usually, it is carried out under exposure. The light source is not limited. Mercury lamp, tungsten lamp, etc., can be used. Also use of a radical initiator such as benzoyl peroxide or 2,2-azobis (isobutylonitrile)., etc., instead of exposure is effective in the improvement of reaction activity. The radical initiator is used in an amount of about 0.001 to 0.01 parts by weight per 1 part by weight of aromatic aldehyde as the raw material.

The reaction temperature is $-10°$ to $80°$ C. and preferably, $0°$ to $50°$ C. The reaction pressure is 5 kg/cm$^2$ or below. Usually, the reaction is carried out under atmospheric pressure.

The shorter the reaction time or the lower the concentration of aromatic aldehyde as the raw material in the reaction liquid is, the more sharply the amount of benzal chlorides to be by-produced is reduced. However, it becomes difficult to remove heat in an industrial apparatus since exothermic due to chlorination reaction is large. Further, when a large amount of solvent is used, production efficiency is lowered.

According to the process of the present invention, the production amount of benzal chlorides as by-products whose separation according to a conventional method such as distillation is difficult, can be reduced sharply by reacting an aromatic aldehyde with chlorine in a liquid phase in the presence of an inert gas, whereby a high purity of benzoyl chlorides can be easily obtained industrially. The industrial significance of the present invention is large.

PREFERRED EMBODIMENTS OF THE INVENTION

Some of the preferred embodiments of the present invention will be described in detail below, referring to examples, which are not intended to limit the scope of the present invention.

EXAMPLE 1

60 g of p-ethylbenzaldehyde and 140 g of o-dichlorobenzene were charged into a flask having a capacity of 500 ml, equipped with a gas blowing pipe, a reflux condenser and a stirrer, and then the temperature of the interior was adjusted to $60°$ C. while introducing therein nitrogen from the gas blowing pipe.

The reaction liquid was bubbled with nitrogen for 1 hour and then feeding of nitrogen was stopped. The reaction was started by beginning both feeding of a mixed gas with a ratio by volume of chlorine to nitrogen 1:1 and light irradiation with a mercury lamp.

30 g of chlorine was fed over 3 hours while maintaining the reaction temperature to $60°$ C. to carry out the reaction and then feeding of chlorine was stopped. The reaction liquid was bubbled with nitrogen for 1 hour.

The reaction product liquid thus obtained was analyzed by gaschromatrgaphy. The conversion of p-ethyl benzaldehyde (hereinafter, referred to as "PEBAL") was 79.4%. The selectivity of p-ethylbenzoylchloride (hereinafter, referred to as "PEBC") was 73.4 mol %. The selectivity of 1-dichloromethyl-4-ethylbenzene (hereinafter, referred to as "DCEB") as benzal chlorides was 0.4 mol %. The selectivity of compounds wherein ethyl group or phenyl group of p-ethylbenzaldehyde was chlorinated (hereinafter, referred to as "CEBAL" was 5.9 mol %. The selectivity of compounds wherein ethyl group or phenyl group of p-ethylbenzoylchloride was chlorinated (hereinafter referred to as "CEBC") was 9.2 mol %.

EXAMPLE 2

The reaction was carried out in the same manner as in Example 1 except a mixed gas with a ratio by volume of chlorine to nitrogen=1:2 was fed during the reaction.

As a result, the conversion of PEBAL was 80.2%. The selectivity of PEBC was 74.4 mol %. The selectivity of DCEB as benzal chlorides was 0.3 mol %. The selectivity of CEBAL was 5.7 mol %. The selectivity of CEBC was 9.2 mol %.

EXAMPLE 3

70 g of p-tolualdehyde and 210 g of o-dichlorobenzene were charged into a flask having a capacity of 500 ml, equipped with a gas blowing pipe, a reflux condenser and a stirrer, and then the temperature of the interior was adjusted to $5°$ C. while introducing therein nitrogen from the gas blowing pipe.

The reaction liquid was bubbled with nitrogen for 1 hour and then feeding of nitrogen was stopped. The reaction was started by beginning both feeding of a mixed gas with a ratio by volume of chlorine to nitrogen 1:1 and light irradiation with a mercury lamp.

38 g of chlorine was fed over 1 hour while maintaining the reaction temperature to $5°$ C. to carry out the reaction and then feeding of chlorine was stopped. The reaction liquid was bubbled with nitrogen for 1 hour.

The reaction product liquid thus obtained was analyzed by gaschromatgraphy. The conversion of p-tolualdehyde was 91%. The selectivity of p-toluoyl chloride was 81.4 mol %. The selectivity of 1-dichloromethyl-4-methylbenzene as benzal chlorides was 0.3 mol %.

COMPARATIVE EXAMPLE 1

The reaction was carried out in the same manner as in Example 1 except only chlorine gas was fed during the reaction. As a result, the conversion of PEBAL was 78.6%. The selectivity of PEBC was 68.1 mol %. The selectivity of DCEB as benzal chlorides was 1.8 mol %. The selectivity of CEBAL was 7.0 mol %. The selectivity of CEBC was 8.9 mol %.

COMPARATIVE EXAMPLE 2

The reaction was carried out in the same manner as in Example 3 except that only chlorine gas was fed during the reaction. As a result, the conversion of p-tolualdehyde was 93%. The selectivity of p-toluoyl chloride was 80 mol %. The selectivity of 1-dichloromethyl-4-methylbenzene as benzal chlorides was 1.5 mol %.

What is claimed is:

1. A process for producing benzoyl chlorides which comprises reacting an aromatic aldehyde with chlorine in a reaction liquid in the presence of inert gas while simultaneously feeding both chlorine-containing gas and the inert gas into the reaction liquid.

2. A process for producing benzoyl chlorides according to claim 1, wherein said reaction is conducted at a temperature of −10° to 80° C. under a pressure of 5 kg/cm² or below.

3. A process for producing benzoyl chlorides according to claim 1, wherein said aromatic aldehyde is represented by the following general formula (I);

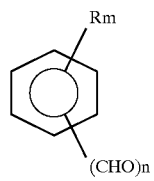 (I)

wherein R shows an alkyl group, a phenyl group, an alkyl-substituted phenyl group, hydrogen or halogen, and m and n are integers of 1 to 5 showing the number of substituted group, m+n≦6, or a mixture of compounds represented by the same general formula (I) as defined above wherein R, m and n the compounds is different from each other.

4. A process for producing benzoyl chlorides according to claim 1, wherein said inert gas is fed to the reaction system in a mixture of chlorine or separately from chlorine.

5. A process for producing benzoyl chloride according to claim 4, wherein an feeding amount of said inert gas is 0.1 to 50 times by mol to that of chlorine.

6. A process for producing benzoyl chloride according to claim 1, wherein said reaction is conducted in the presence of a solvent selected from the group consisting of o-dichlorobenzene, chlorobenzene, carbon tetrachloride and benzonitrile.

* * * * *